United States Patent
Rocklin et al.

(10) Patent No.: US 7,111,501 B2
(45) Date of Patent: Sep. 26, 2006

(54) DEVICES AND METHODS FOR SEPARATING CONSTITUENTS

(75) Inventors: Roy D. Rocklin, Sunnyvale, CA (US); Kevin P. Killeen, Palo Alto, CA (US); Hongfeng Yin, Cupertino, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 121 days.

(21) Appl. No.: 10/678,332

(22) Filed: Oct. 3, 2003

(65) Prior Publication Data
US 2005/0072671 A1 Apr. 7, 2005

(51) Int. Cl.
G01N 30/00 (2006.01)
(52) U.S. Cl. .................... 73/61.52; 73/53.01
(58) Field of Classification Search .............. 73/61.52, 73/53.01, 61.41, 61.43, 61.53
See application file for complete search history.

(56) References Cited

U.S. PATENT DOCUMENTS

| | | | |
|---|---|---|---|
| 4,399,036 A | 8/1983 | Babb et al. | |
| 5,690,893 A * | 11/1997 | Ozawa et al. | 422/67 |
| 6,046,056 A | 4/2000 | Parce et al. | |
| 6,860,137 B1 * | 3/2005 | Kitagawa | 73/1.02 |
| 2001/0048958 A1 | 12/2001 | Funk | |
| 2002/0129664 A1 | 9/2002 | Jorgenson et al. | |
| 2003/0047680 A1 | 3/2003 | Figeys et al. | |
| 2004/0195099 A1 * | 10/2004 | Jacobson et al. | 204/450 |

FOREIGN PATENT DOCUMENTS

EP 1143238 A2 * 10/2001

* cited by examiner

Primary Examiner—Hezron Williams
Assistant Examiner—Rodney Frank

(57) ABSTRACT

The subject invention includes constituent separation apparatuses that include a fluid pathway and a pair of spaced-apart electrodes positioned within the pathway for detecting current flow within a mobile phase present in the pathway. Coupled to the pair of spaced-apart electrodes is a mix ratio determinator for determining the mix ratio of the mobile phase from the detected current flow. Also provided are methods that include contacting a mobile phase with an apparatus for separating constituents of a mobile phase, detecting the current flow of the mobile phase when the mobile phase is in contact with the apparatus and determining the mix ratio of the mobile phase from the detected current flow. The mix ratio may be adjusted based on the determined mix ratio. Algorithms for practicing the subject methods are also provided on computer readable mediums. Systems and kits for practicing the subject methods are also provided.

32 Claims, 5 Drawing Sheets

DEVICES AND METHODS FOR SEPARATING CONSTITUENTS

FIELD OF THE INVENTION

The field of this invention is analytical chemistry, and more specifically analytical chemistry involving a mobile phase.

BACKGROUND OF THE INVENTION

The goal of many analytical chemistry protocols is to separate a sample (blood, tears, urine, water from a well, etc.) into its individual components or constituents so that each component may be evaluated without any interference from other components. A variety of techniques have been developed for this task and include electrophoretic protocols, chromatographic protocols, and the like. Once the constituents have been separated, they can be detected by various techniques, e.g., refractive index, electrochemical, or ultraviolet-absorbance, which can indicate the presence of a given constituent. The amount of constituent may be determined by the intensity of the signal produced in a detector. A detector is employed to measure a signal peak as each constituent exits the column and may be "on-line" or "off-line" (i.e., integral with the separation apparatus or a separate component thereof, respectively). By comparing the time it takes for the peak to show up (also referred to as the retention time) with the retention times for a mixture of known compounds, the constituents of unknown sample mixtures can be identified. By measuring the signal intensity (also referred to as the response) and comparing it to the response of a known amount of that particular analyte, the amount of analyte in the mixture can be determined.

For example, one technique that is often employed to separate various constituents of a sample from each other is chromatography, where liquid chromatography ("LC") is often employed. Liquid chromatography is an analytical chromatographic technique that is useful for separating ions or molecules that are dissolved in a liquid or solvent. If the sample solution is in contact with a second solid or liquid phase, the different solutes will interact with the other phase to differing degrees due to differences in adsorption, ion-exchange, partitioning, or size. These differences allow the mixture components to be separated from each other by using these differences to determine the transit time of the solutes through a column. Chromatography may be coupled with a suitable on- or off-line detection system that can characterize each type of separated constituent. One liquid chromatography protocol that is often employed due to its versatility is high performance liquid chromatography ("HPLC"). Generally, HPLC includes passing a sample of constituents in a high pressure fluid or solvent (called the mobile phase) through a tube or column. The column is packed with a stationary phase. The stationary phase is typically composed of a substrate or matrix such as particles, e.g., porous beads or the like. The pore sizes can be varied to allow certain sized analytes to pass through at different rates. As the constituents pass through the column they interact with the mobile and stationary phases at different rates. The difference in rates is due to the difference in one or more physical properties of the constituents, e.g., different polarities. The constituents that have the least amount of interaction with the stationary phase, or the most amount of interaction with the mobile phase, will thus exit the column faster.

One particularly useful mode of HPLC—particularly for the separation of highly polar or ionizable constituents, is reversed phase high performance liquid chromatography ("RP-HPLC"). RP-HPLC primarily operates on the basis of hydrophilicity and lipophilicity to separate various constituents of a liquid medium from each other. The stationary phase includes a substrate (which may be a plurality of particles) that has bound chemical moieties (i.e., a bonded phase), such as hydrophobic chains, e.g., bound alkyl chains, and the like, which facilitate the separation of the constituents. Accordingly, the greater the hydrophobicity of the bound chemical moieties, the greater is the tendency of the hydrophobic constituents in the mobile phase to be retained in the column while the hydrophilic constituents are eluted more rapidly from the column than the hydrophobic constituents.

Regardless of the analytical protocol or technique employed, oftentimes the sample of interest is associated with a fluid, i.e., a mobile phase, prior to the actual separation step, e.g., prior to being contacted with a matrix or solid phase such as a chromatographic column or channel or the like, e.g., a capillary channel such as employed in a microfluidic device. The mobile phase is often a particular ratio mix of two or more fluids and in many instances the mix ratio of the fluids of the mobile phase changes over the course of a particular protocol, e.g., to provide a gradient of the mobile phase over time. For example, in many protocols a mobile phase is composed of a mix of an organic solvent and an aqueous solvent, where in certain instances it may be desirable to vary the ratio of the two solvents over the course of the protocol to provide a gradient, e.g., gradually or step-wise. Accordingly, regardless of the type of analytical protocol employed, it is critical to the outcome of the protocol to know and maintain a particular mix ratio of the mobile phase at any given time point during a protocol.

However, it is difficult to determine the mix ratio of the mobile phase, e.g., prior to, during and/or after the separation step, to ensure the proper mix ratio is employed and/or to monitor the mix ratio, where such is particularly relevant in gradient elution wherein the mix ratio changes over time throughout a protocol and it is important to understand what the particular mix ratio is at a given time point of time. Although the mix ratio is known at the source (e.g., the pump that is used to deliver the fluid to the system), there is a delay between the setting of the mix ratio at the source and the time the ratio reaches the separation apparatus or a particular area of the separation apparatus such as the area where separation actually takes place, e.g., a separation column or channel. Accordingly, in order to know the exact conditions of a given separation protocol, the mix ratio must be measured at (i.e., on) the device itself- in other words in "real time".

Accordingly, there continues to be an interest in the development of new methods and apparatuses for determining the mix ratio of a mobile phase. Of particular interest is the development of such methods and apparatuses that determine the mix ratio directly on a separation apparatus itself, are easy to use, and have a high degree of precision.

References of interest include: U.S. Pat. Nos. 4,399,036; 4,908,112; 5,770,029; 5,755,942; 5,746,901; 5,681,751; 5,658,413; 5,653,939; 5,653,859; 5,645,702; 5,605,662; 5,571,410; 5,543,838; 5,480,614; 6,046,056; 6,143,248; 6,158,712; 6,296,452; 6,375,901; 6,431,212; 6,495,016; 6,533,553; 6,561,224; and U.S. patent applicant Ser. Nos. 2003/0000835 and 2001/0048958. Also of interest are: Knox et al. (1987) Chromatographia 24:135); Peters et al. (1998) Anal. Chem. 70:2288); Hadd, et al., Microchip device for performing enzyme assays. Analytical Chemistry 69, 3407–3412 (1997); Macounova, et al. Concentration and separation of proteins in microfluidic channels on the basis of transverse IEF. Analytical Chemisty 73, 1627–1633 (2001); and Bucholz, et al. Microchannel DNA sequencing matrices with a thermally controlled "viscosity switch". Analytical Chemisty 73, 157–164 (2001).

SUMMARY OF THE INVENTION

The subject invention includes constituent separation apparatuses that include a fluid pathway and a pair of spaced-apart electrodes positioned within the pathway for detecting current flow within a mobile phase present in the pathway. Coupled to the pair of spaced-apart electrodes is a mix ratio determinator for determining the mix ratio of the mobile phase from the detected current flow. Also provided are methods that include contacting a mobile phase with an apparatus for separating constituents of a mobile phase, detecting the current flow of the mobile phase when the mobile phase is in contact with the apparatus and determining the mix ratio of the mobile phase from the detected current flow. The mix ratio may be adjusted based on the determined mix ratio. Algorithms for practicing the subject methods are also provided on computer readable mediums. Systems and kits for practicing the subject methods are also provided.

BRIEF DESCRIPTIONS OF THE DRAWINGS

Figure 3:
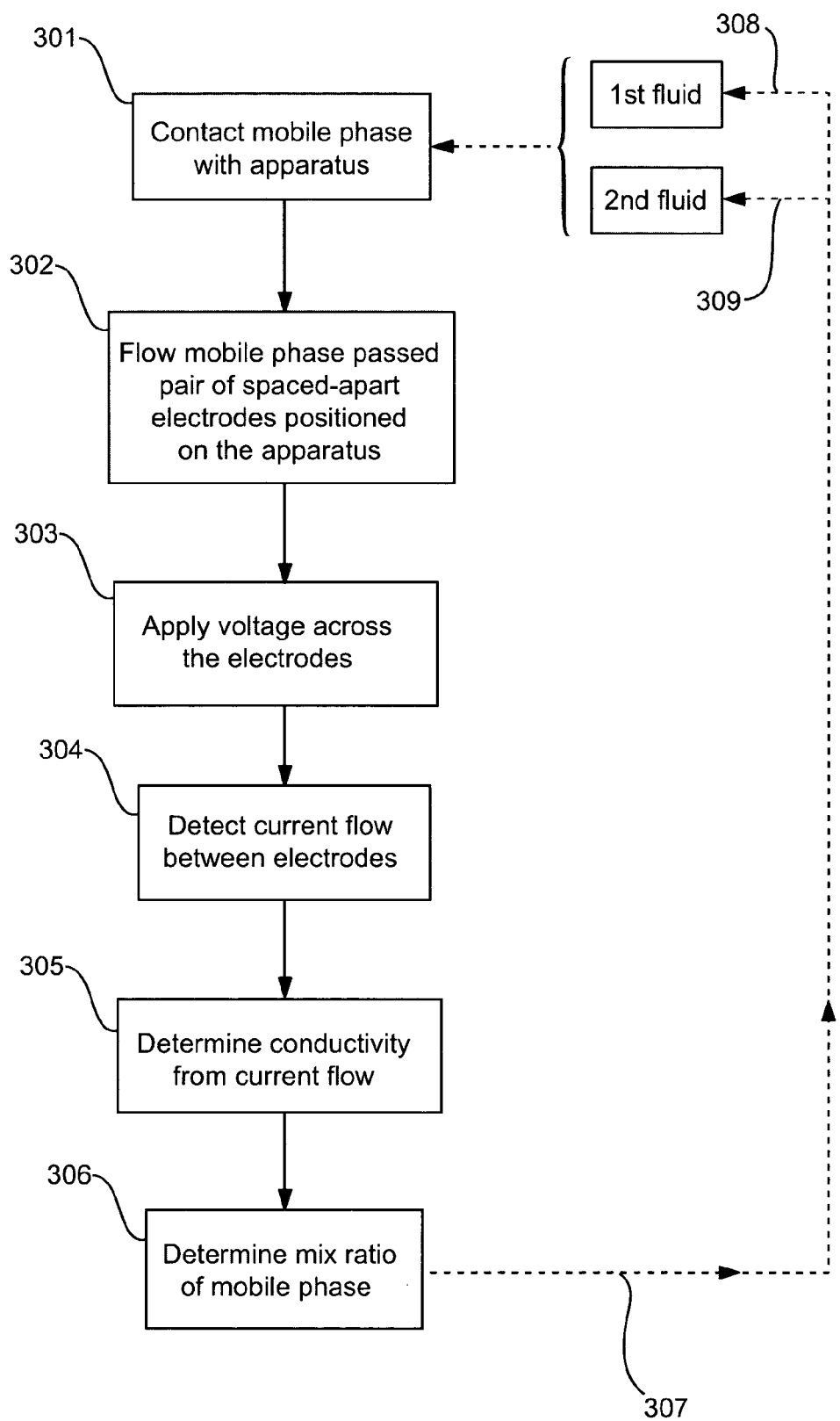

FIG. 3 provides a flowchart describing steps of the subject methods.

Figure 4:
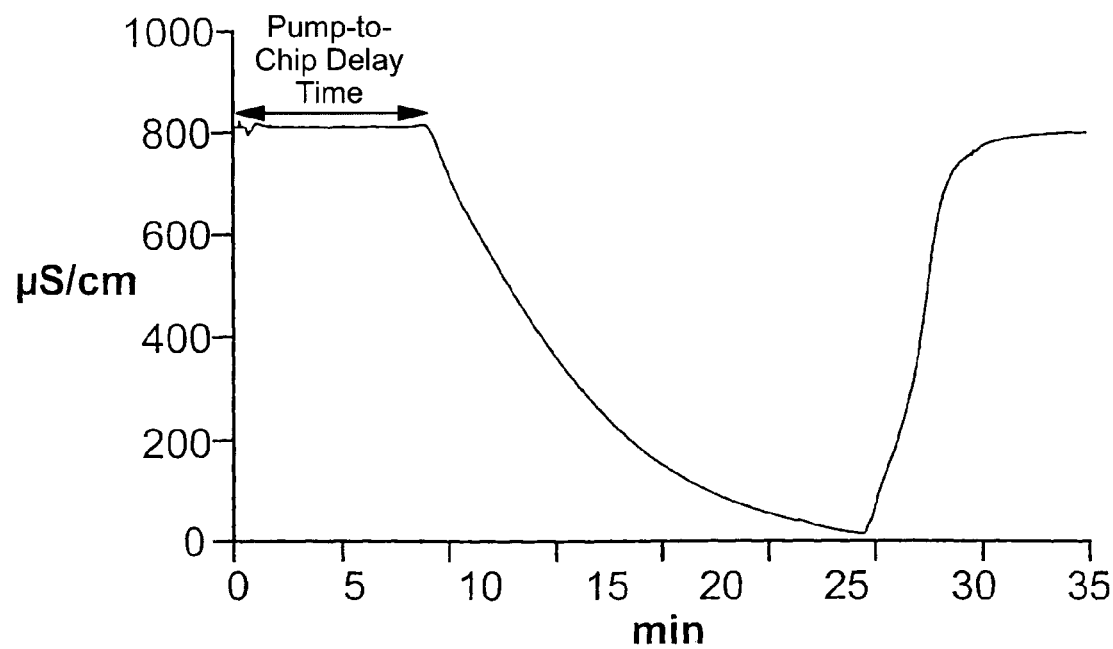

FIG. 4 shows a graphical representation of results produced by practicing the subject invention whereby the proportions of the different fluids of the mobile phase are changed in a gradient or gradual manner over time.

Figure 5:
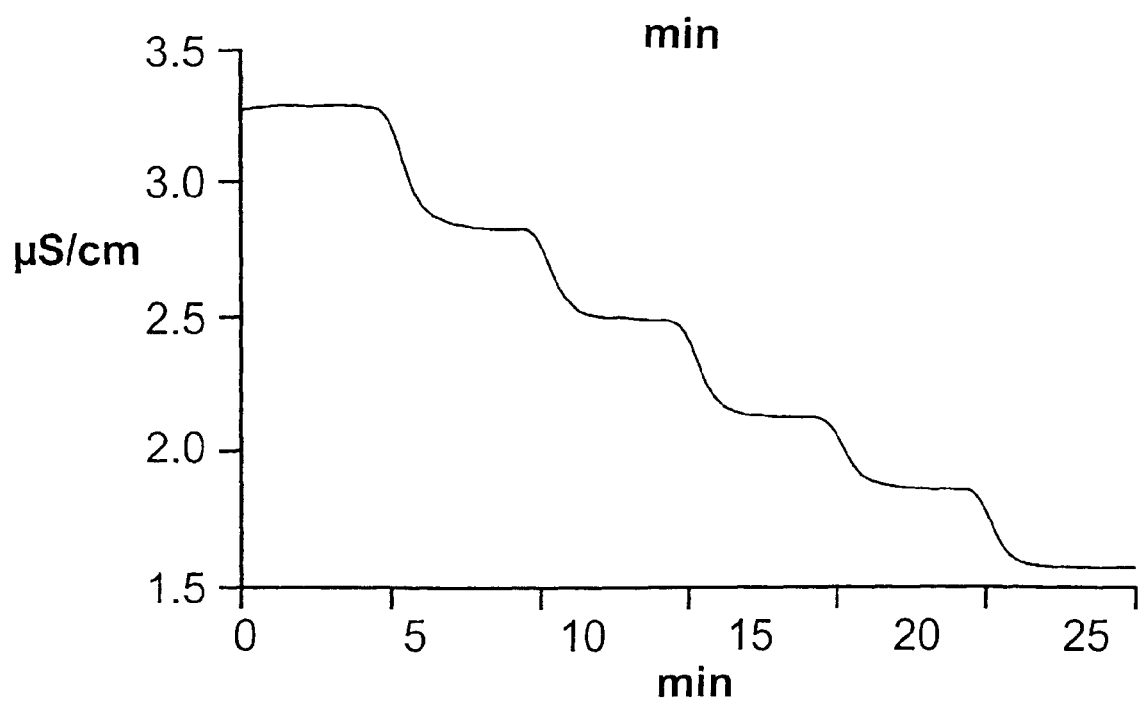

FIG. 5 shows a graphical representation of results produced by practicing the subject invention whereby the proportions of the different fluids of the mobile phase are changed in a stepwise manner over time.

Figure 6:
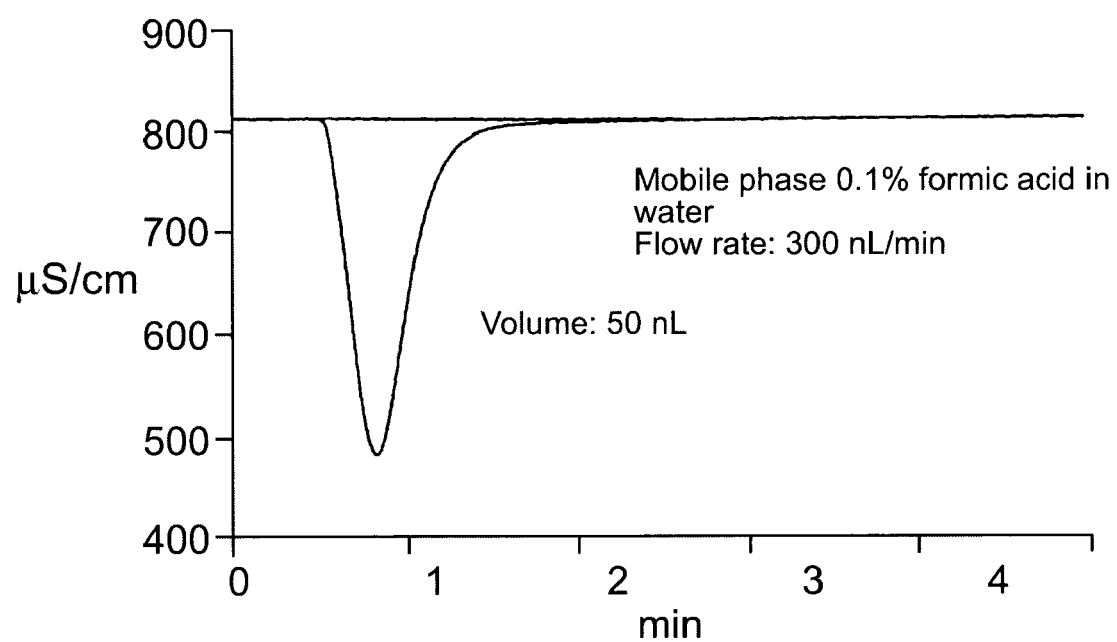

FIG. 6 shows a graphical representation of results produced by practicing the subject invention to determine injection loop volume.

DETAILED DESCRIPTION OF THE INVENTION

The subject invention includes constituent separation apparatuses that include a fluid pathway and a pair of spaced-apart electrodes positioned within the pathway for detecting current flow within a mobile phase present in the pathway. Coupled to the pair of spaced-apart electrodes is a mix ratio determinator for determining the mix ratio of the mobile phase from the detected current flow. Also provided are methods that include contacting a mobile phase with an apparatus for separating constituents of a mobile phase, detecting the current flow of the mobile phase when the mobile phase is in contact with the apparatus and determining the mix ratio of the mobile phase from the detected current flow. The mix ratio may be adjusted based on the determined mix ratio. Algorithms for practicing the subject methods are also provided on computer readable mediums. Systems and kits for practicing the subject methods are also provided.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The figures shown herein are not necessarily drawn to scale, with some components and features being exaggerated for clarity.

In further describing the subject invention, the subject analytical apparatuses are described first in greater detail, followed by a review of the subject methods. Finally, kits for use in practicing the subject methods are described.

Apparatuses

As summarized above, the subject invention includes constituent separation apparatuses for separating or otherwise analyzing constituents of a mobile phase. In general, the subject apparatuses include a mobile phase fluid pathway for transporting a mobile phase from a first area of the apparatus to a second area of the apparatus. Present within this mobile phase fluid pathway is a pair of spaced-apart electrodes for detecting the current flow of a mobile phase present in the pathway. Operatively coupled to the pair of spaced-apart electrodes is a mobile phase mix ratio determinator, e.g., a processor or series of processors under the control of a software program, that is capable of executing the steps necessary to determine the mix ratio of the mobile phase based on the current flow detected by the electrodes present in a fluid pathway. In certain embodiments a feedback loop is provided for automatically adjusting the mix ratio of the mobile phase in response to the detected current flow and more specifically the determined mix ratio.

The subject invention is suitable for a variety of different chemical, physical and/or biological analysis or synthesis apparatuses and technologies that employ a mobile phase (i.e., a fluid phase), e.g., eletrophoretic, chromatographic, electrochromatographic, and the like. In this regard, "chromatographic" processes generally encompasses preferential separations of components using protocols based on, e.g., liquid chromatography, high performance liquid chromatography, reversed-phase liquid chromatography, hydrophobic interaction, ion exchange, molecular sieve chromatography, affinity chromatography and like. "Electrophoretic" separations generally refers to the migration of particles or macromolecules having a net electric charge where said migration is influenced by an electric field. Accordingly electrophoretic separations contemplated for use in the invention include, e.g., separations performed in columns, channels or fluid pathways packed, coated or lined with gels or other suitable matrices (such as poly-acrylamide, agarose and combinations thereof) as well as separations performed in solution. "Electrochromatographic" separations refer to combinations of electrophoretic and chromatographic techniques. Electrochromatographic separations are a hybrid technique typically, though not always, performed in microcapillary format. Column or channel packing may be either traditional packed column (see, e.g., Knox et al. (1987) Chromatographia 24:135) or monolithic packing (see, e.g., Peters et al. (1998) Anal. Chem. 70:2288).

Accordingly, the subject apparatuses may be employed for a wide variety of protocols including, but not limited to, separation, purification, biomolecular signaling, cellular response, enzymatic interactions, binding assays and the like (e.g., cellular signaling, antibody-antigen interactions, enzyme-substrate interactions, receptor-ligand interactions, etc.). In other words, the subject apparatuses may be employed and/or adapted for use with any chemical, physical and/or biological technology that employs a mobile phase to process, separate and/or analyze at least one constituent of interest present in, or suspected of being present in, the mobile phase.

While the subject invention is described primarily with reference to those apparatuses that utilize chromatographic techniques to separate constituents, it is to be understood that such is for ease of description only and it not intended to limit the subject invention in any way. Accordingly, in many embodiments the subject devices are chromatography apparatuses, such as liquid chromatography ("LC") apparatuses, and in certain embodiments the subject methods are high performance liquid chromatography ("HPLC") apparatuses, where in certain embodiments the subject devices are reversed phase high performance liquid chromatography ("RP-HPLC") devices. In certain other embodiments, the subject apparatuses are electrophoresis apparatuses, e.g., capillary electrophoresis and the like. It will also be apparent to those of skill in the art that the subject invention may be employed with analytical apparatuses that perform functions other than, or in addition to, constituent separation, as will be described in greater detail below. The novel positioning of the electrodes of the subject invention, i.e., by utilizing electrodes positioned in a fluid pathway on the subject apparatus itself, enables the determination of the mix ratio of a mobile phase in "real-time", i.e., while the mobile phase is present on the apparatus.

The subject apparatuses may be configured to separate or analyze a variety of organic and inorganic constituents or analytes as will be apparent to those of skill in the art. That is, a wide variety of constituents may be processed, separated and/or analyzed according to the subject invention, where the subject apparatuses may be configured to separate or analyze non-polar, polar, e.g., highly polar, and ionic constituents, sometimes in the same separation process. The constituents may be naturally occurring or synthetic, and may be pre-processed or otherwise manipulated prior to separation by the subject invention. Representative constituents include, but are not limited to, proteins, peptides, polypeptides, glycoproteins, saccharides (mono- poly- and oligo-saccharides) nucleic acids, lipids, phospholipids, fullerene compounds, glycolipids, carboxylic acids, vitamins, catecholamines, purines, pyrimidines, nucleotides, various polar pharmaceuticals, or other suitable substances that can be analyzed using a mobile phase. In certain embodiments, a constituent may be derivatized such that an easily detectable chemical group may be attached to the constituent, e.g., to make the constituent easy to detect either on the apparatus itself in the case of "on-line" detection or once it emerges from the apparatus in the case of "off-line" detection. Examples of such derivatization processes include, but are not limited to, attaching an ultraviolet absorbing group to a constituent, attaching a fluorescent group to a constituent, attaching an electrochemical group to a constituent, etc.

The size of a given apparatus according to the subject invention may vary widely depending on the particular analytical protocol performed and as such range in size from small scale or miniaturized apparatuses, e.g., those known in the art as microfluidic apparatuses, that include pathways or channels of extremely small dimensions to larger apparatuses sometimes referred to as bench scale apparatuses such as bench chromatography apparatuses, e.g., that employ chromatography columns that may be as large as about 3000 cm or more in length and have an internal diameter of about 250 cm or more.

Figure 1:
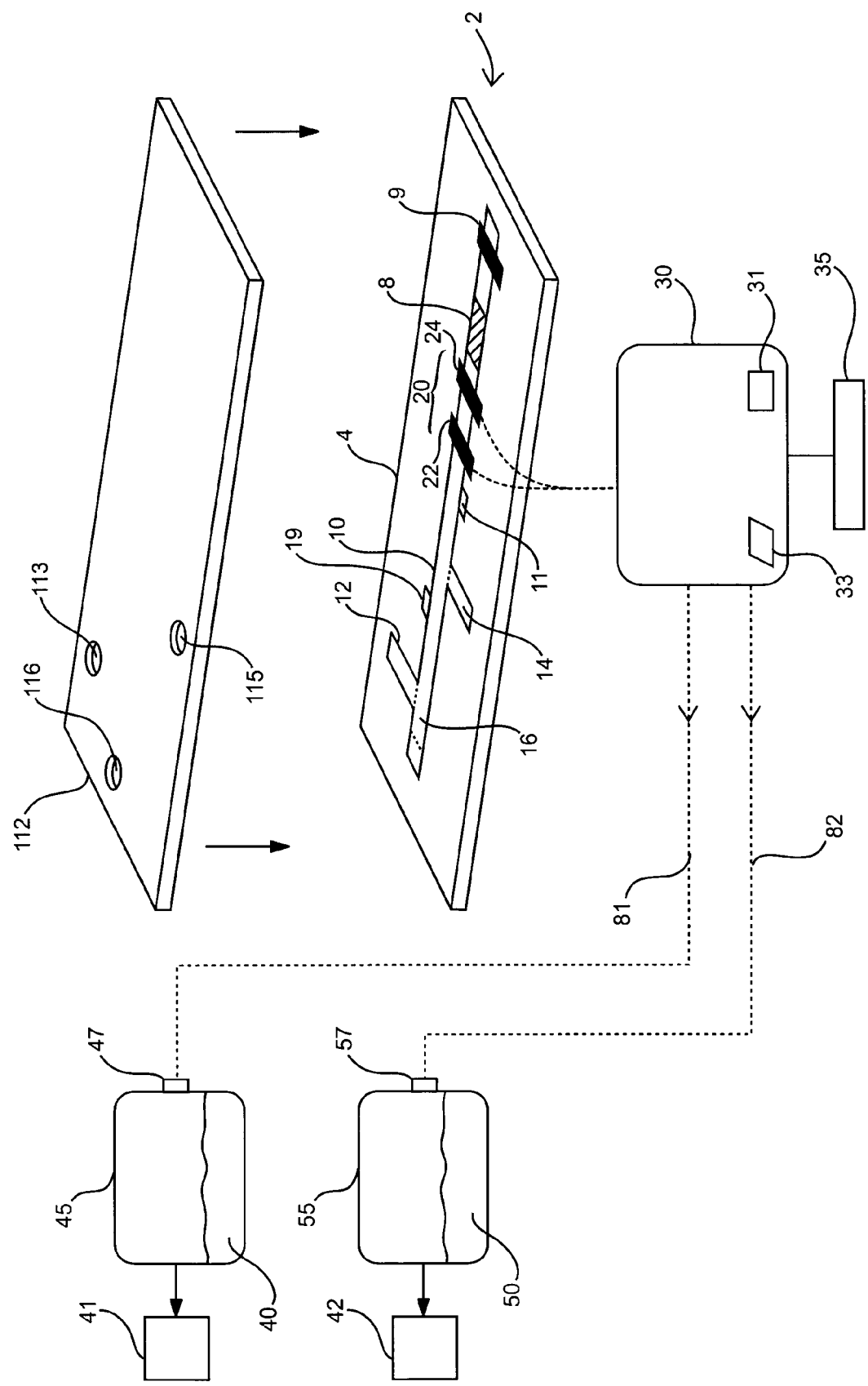
FIG. 1 shows an exemplary embodiment of an apparatus of the subject invention.

FIG. 1 shows a plan view of an exemplary embodiment of a microfluidic apparatus 2 according to the subject invention. By "microfluidic" it is meant that the apparatus includes one or more fluid pathways or channels, conduits, or reservoirs that has at least one dimension, e.g., depth, width, length, etc., that is less than about 500 μm, and typically such a dimension ranges from about 0.01 μm to about 500 μm.

Microfluidic apparatus 2 includes at least one substrate 4 that is typically planar, but may be non-planar in certain embodiments, e.g., it may include surface modifications, structures, and the like such as ridges, ledges, bumps, etc., thereon. The material of substrate 4 is chosen to be compatible with the particular chemical or biochemical analyses with which the apparatus is intended to be used, e.g., compatible with the conditions thereof such as pH, temperature, application of electric fields, etc. Furthermore, since these devices are microfabricated using such techniques as photolithography, deep reactive ion etching ("DRIE"), electroforming, laser ablation, air abrasion, wet chemical etching, embossing, casting, imprinting, injection molding and the like, the material of apparatus 2 is also typically chosen to be compatible with the particular microfabrication technique employed.

Materials of interest that may be employed in the fabrication of substrate 4 include, but are not limited to, silica-based substrates such as glass, ceramic, quartz, silicon or polysilicon and other materials such as metals and polymeric materials, e.g., such as ABS (acrylonitrile-butadiene-styrene copolymer), polysulfone, polystyrene, polymethylpentene, polypropylene, polyethylene, polymethylmethacrylate (PMMA), polyvinylchloride (PVC), polyvinylidine fluoride, polydimethylsiloxane (PDMS), polycarbonate, polytetrafluoroethylene (TEFLON®), polyurethane, polyfluorcarbons, polyimide, polyester, polyamide, polyether, polyolefin, and the like, and mixtures thereof. The substrates of the subject invention may be composites, laminates, etc. A "composite" is a composition comprised of different materials. The composite may be a block composite, e.g., an A-B-A block composite, an A-B-C block composite, or the like. Alternatively, the composite may be a heterogeneous, i.e., in which the materials are distinct or in separate phases, or homogeneous combination of different materials. As used herein, the term "composite" is used to include a "laminate" composite. A "laminate" refers to a composite material formed from several different bonded layers of same or different materials. Other composite substrates include polymer laminates, polymer-metal laminates, e.g., polymer coated with copper, a ceramic-in-metal or a polymer-in-metal composite. At least a portion of the apparatus, e.g., the area around the pair of electrodes 20, may include an insulating layer, e.g., if the substrate is not an insulator, film or coating such as silicon oxide or the like and/or surfaces that have been treated, e.g., coated or derivatized and the like, to optimize utility in microfluidic protocols such as to enhance fluid mobility, e.g., to render a surface hydrophobic, hydrophilic, lipophilic, lipophobic, etc.

In many embodiments, embodiments of the microfluidic apparatuses may include at least one other substrate or coverplate that is mateable or joinable to substrate 4 so as to lie, e.g., on top of, or align with substrate 4 when fit together. Together the mateable substrates provide the channels, ports, reservoirs, etc., of the apparatus. The second substrate layer may be removably or fixably aligned over the first substrate to form a liquid-tight separation compartment by using pressure sealing techniques, by using external means to urge the pieces together (such as clips, tension springs or associated clamping apparatus) or by using adhesives well known in the art of bonding polymers, ceramics, glass, metal, composites, laminates, and the like. Although illustrated as a separate component, it will be recognized by a person of skill in the art that the cover plate may be hingeably affixed to the substrate. Accordingly, in such embodiments substrate 4 may be characterized as a "bottom" substrate and at least one other substrate associated therewith may be characterized as a "top" substrate 112- or vice versa and, regardless of which is referred to as the top or bottom, together the top and bottom substrates define or provide for an interior portion having fluid pathways, analytical matrices (if employed), spaced-apart electrodes, etc. In the present application, unless a contrary intention appears, terms such as "top" and "bottom" are used in a relative sense only, although they indicate a typical (though not essential) orientation during apparatus use.

While the embodiment of FIG. 1 has a rectangular shape, a subject apparatus may have a number of different shapes ranging from simple to complex such as square, circular, oblong, triangular, polygonal, etc., or more complex or irregular shapes. The size of a microfluidic apparatus of the subject invention may vary depending on a variety of factors such as the particular chemical or biochemical protocol being performed, the number of fluid pathways, etc. In many embodiments, the length of substrate 4 may range from about 1 mm to about 200 mm, e.g., from about 5 mm to about 100 mm, the width of substrate 4 may range from about 1 mm to about 200 mm, e.g., from about 5 mm to about 100 mm and the thickness of substrate 4 may range from 10 µm to about 10 mm, e.g., from 25 µm to about 5 mm. In those embodiments having more than one substrate layer as described above, the total thickness of the apparatus typically, though not always, does not exceed about 20 µm to about 20 mm, e.g., is usually less than about 50 µm to about 10 mm. Apparatuses having shapes such as circular, oblong and the like have analogous dimensions.

The microfluidic apparatuses of the subject invention include at least one microfluidic mobile phase fluid pathway or microchannel disposed therein for the transport of a mobile phase used in the analysis from a first location to a second location. The number of fluid pathways of a given microfluidic device may range from one to a few to hundreds of fluidly connected fluid pathways such that certain embodiments may only have one mobile phase fluid pathway and certain embodiments may include a network of intersecting fluid pathways. Fluid pathways may be fabricated, e.g., using a microfabrication process described above, into a surface of substrate 4. In microfluidic apparatus 2, main mobile phase fluid pathway 10 is shown, as are pathways 12, 14 and 16 which intersect pathway 10 so as to provide fluid communication therebetween such that fluid in these types of pathways may merge into the main mobile phase fluid pathway. Intersections may exist in a number of configurations and geometries such as "T" intersections, "wagon-wheel" intersections, cross intersections and the like.

The fluid pathways are configured to enable introduction of various fluids to the apparatus independent of one another, but also to enable one or more of the introduced fluids to meet or combine at some point on the apparatus, as noted above. As used herein, a "fluid" references a liquid. In a protocol wherein a mobile phase is made-up of two different fluids, a particular amount of a first mobile phase fluid may be contacted with main mobile phase pathway 10 via pathway 12, a contacted with main mobile phase pathway 10 via pathway 16 and the first and particular amount and/or concentration of a second mobile phase fluid may be second fluids are thereby able to meet and combine in fluid pathway 10 to provide a mobile phase having an appropriate mix ratio of the two fluids for a given protocol. In this manner, the proportion of the individual components of the mobile phase may be altered, e.g., gradually or step-wise, during a given protocol by adjusting the amount of fluid allowed to flow from a given reservoir. The supply from each reservoir may pass, e.g., to a pump or to a valved mixing element. For example, the fluid mixing may occur at high pressure or the fluids may be premixed at low pressure and then passed to a pump. For example, in certain embodiments, the speed of a respective pump may be precisely controlled by the frequency of its power supply and the frequency may be controlled by external oscillators or directly from a computer-based apparatus. In certain other embodiments, the solvent from each reservoir is passed to a valve, the output from which is connected to a mixing element. The mixing element receives and mixes solvents from each of the programmed valves which are electrically operated and programmed to open and close for different periods of time by adjusting the frequency and wave form of the supply. Accordingly, a predetermined and precisely controlled amount of each solvent is allowed to flow into the mixing element. The valves may be driven by external oscillators or a computer based apparatus that modifies the frequency and wave form to control the flow of each solvent to the apparatus. Of interest is the use of an integrated fluid injection system, as described in U.S. Pat. No. 6,495,016, the disclosure of which is incorporated by reference, where such systems have the advantage being controlled exclusively by the application of an electrical potential, and an electrical voltage in particular, and accordingly require no moving parts at all. In such embodiments, the subject apparatuses include a power supply, i.e., a voltage source/controller. Fluid may be moved through the microchannels using any suitable process or motive force, where such processes are known in the art. The term "motive force" is used herein to refer to any process and technology for inducing movement of a fluid along a channel or column in a liquid phase analysis, and includes application of an electric potential across any portion of the column, application of a pressure differential across any portion of the column or any combination thereof. For example, fluid movement may be accomplished by use of various electro-kinetic processes such as electrophoresis or electro-osmosis. Fluids may be propelled through the very small channels of the subject microfluidic apparatuses by electro-osmotic forces. An electro-osmotic force is built up in the channel via surface charge buildup by means of an external voltage that can "repel" fluid and cause flow. This surface charge and external voltage produces an electro-kinetic current that results in fluid flow along the channel. Such electro-kinetic processes known in the art, for example as described in U.S. Pat. No. 4,908,112, the disclosure of which is herein incorporated by reference.

For example, a first reservoir may contain a first fluid such as 100% water and a second reservoir may contain a second fluid such as an organic modifier (including alcohol based chemicals) such as, but not limited to, methanol, heptafluorobutyric acid (HFBA), acetonitrile, formic acid, N,N'-diethylamine (DEA), tetrahydrofuran, trifluoroacetic acid (TFA), acetone, dichloromethane, hexane, n-heptane, propanol, and the like. In use, the fluids contained in the reservoirs may be combined in a particular proportion to be used throughout the entire separation process or may be combined in various proportions, where the proportion may vary at different times throughout the separation process such that a first fluid may be 100% water, where such may be followed by various fluids of decreasing proportions of water and increasing proportions of an organic modifier, such as 95% water and 5% organic solvent, 90% water and 10% organic solvent, etc.

Sample containing or suspected of containing at least one constituent of interest, may be introduced to the apparatus via any one of the pathways such as pathway 14 which may be positioned in any convenient location about the apparatus, or may be introduced via one of the mobile phase fluid pathways 12 or 16 either before, during or after the introduction of one of the mobile phase fluid components. Alternatively, the mobile phase may be mixed at a point remote from the apparatus and thus introduced to pathway 10 in a mixed state. Accordingly, the constituents of interest, i.e. to be separated, may be added to the reservoirs, but are typically combined with the mobile phase at a downstream location using a introduction syringe or valve such that the constituents are added to the mobile phase at a point after the mobile phase is mixed to provide the suitable mix ratio to be used. Regardless of the number of reservoirs employed, typically each may be coupled to an outgassing element (not shown) for degassing the fluid contained in the reservoir.

The fluid pathways of microfluidic devices are dimensioned to enable analytical protocols that utilize submicroliter, nanoliter and even picoliter amounts of fluids. In the subject microfluidic apparatuses, at least one pathway has a dimension, e.g., depth, width, length, diameter, etc., that is less than about 500 µm, and typically ranges between about 0.1 µm to about 500 µm, and in many embodiments all of the fluid pathways are so dimensioned. For example, a fluid pathway of the subject invention may have a depth that ranges from about 0.1 µm to about 500 µm, e.g., from about 1 µm to about 250 µm, and/or a width that may range from about 0.1 µm to about 500 µm, e.g., from about 1 µm to about 250 µm and/or a length that may range from about 1 µm to about 500 mm, e.g., from about 10 µm to about 200 mm.

In many embodiments, at least a portion 8 of the fluid pathway includes an analytical portion or compartment or reaction chamber within which the processing, including separation processes, of a constituent from the mobile phase is performed. Accordingly, this analytical portion or compartment or reaction chamber is used herein to refer to a region of the apparatus in which sample processing, separation, etc., and usually analytical sample separation, is carried out. "Analytical separation" may be defined as the final separation of analyte from minor components before final analyte detection. In particular, an analyte or constituent (herein used interchangeably) of interest is generally obtained in a mixture containing other species which may potentially interfere with the detection and analysis of the analyte. Accordingly, this area of the apparatus is a region in which analyte separation from other species may be effected. Examples of functions which may be served by the sample treatment component include chromatographic separations, electrophoretic separations, electrochromatographic separations, and the like.

In many embodiments the separation portion may include at least one component that facilitates the particular analysis. Any suitable analytical components(s), moiety or matrix may be employed depending on the particular protocol being performed. In certain embodiments, the analytical component is a stationary phase. By "stationary phase" is meant the immobile phase involved in the separation process, e.g., a chromatographic process. A stationary phase may include a solid support alone or a solid support with a bonded phase, where the bonded phase is attached, associated, connected or otherwise coupled or linked to the solid support. The immobile phase may be contrasted with the mobile phase or eluent, i.e., the liquid phase. The stationary phase may be a solid, a bonded or coated phase on a solid support, or a wall-coated phase. In many embodiments, the stationary phase is made up of a plurality of particles, e.g., as is known in the art, for example as employed for HPLC protocols, and may be porous. If porous, the average pore size and total porosity of a given stationary phase, i.e., the ratio of the volume of interstices to the volume of the solid particles, is chosen to optimize the particular separation procedure being performed. The porosity of a given stationary phase of the subject invention may vary depending on the particular separation protocol being performed. A variety of materials may be employed for the stationary phase, where suitable materials include, but are not limited to, magnetic particles, silica (e.g., $SiO_2$), alumina (e.g., $Al_2O_3$), any other suitable metal oxides including transition metal oxides, as well as polymeric materials such as poly(styrene-divinylbenzene) (PS-DVB), cellulose, sugar polymers (e.g., agarose, dextran), silica-coated polymers, organo modified metal or transition metal oxides (hybrid) and continuous metal oxide or chemically modified metal oxide monolithic structures. In certain embodiments, the stationary phase may be a biomolecule or other pre-disposed assay or analysis component. For example, the portion may include a member of a particular binding pair, e.g., a ligand or receptor, antigen or antibody, nucleic acid for hybridization reactions, enzyme or receptor, etc. This separation portion may also include particular reactants or reagents such as protein or nucleic acid digestive agents, surfactants, etc.

A surface of the reaction portion of the apparatus, or of a component thereof (e.g., a stationary phase thereof), may be treated to provide a surface treatment for facilitating a particular constituent separation. The term "surface treatment" is used to generally refer to preparation or modification of the surface of a substrate (i.e., the walls of a fluid pathway, a stationary phase, etc.) that will be in contact with a sample during separation, whereby the separation characteristics of the apparatus are altered or otherwise enhanced. Accordingly, "surface treatment" as used herein includes: physical surface adsorptions; covalent bonding of selected moieties to functional groups on the surface of treated substrates (such as to amine, hydroxyl or carboxylic acid groups on condensation polymers); methods of coating surfaces, including dynamic deactivation of treated surfaces (such as by adding surfactants to media), polymer grafting to the surface of treated substrates (such as polystyrene or divinyl-benzene) and thin-film deposition of materials such as diamond or sapphire to treated substrates.

In those embodiments having a second substrate 112, usually the substrate 112 includes one or more ports that traverse the thickness of the second substrate and which are positioned to be aligned with, or more specifically in communication with, respective fluid channels of substrate 4. These ports provide access points for the introduction of fluids, e.g., sample, mobile phase fluids, etc., to a respective fluid pathway of the apparatus. In many embodiments, these ports are sealable ports, e.g., self-sealing, so as to minimize contamination of the fluids introduced to the interior of the apparatus from the exterior environment of the apparatus. For example, a port may include a re-sealable gasket or the like that closes back in on itself after being breached by a needle, pipette tip, etc. Of course, in the absence of a second substrate, fluids may be introduced directly to the pathways of substrate 4.

As noted above, a feature of the subject apparatuses is the inclusion of elements for the determination of the mix ratio of the mobile phase. Accordingly, a subject apparatus includes a conductance sensor 20 that is operatively coupled (represented as dashed lines between the sensor 20 and mix ratio determinator 30) to a mobile phase mix ratio determinator 30 which includes at least one processor 31 under the control of a computer program which directs the processor(s) to execute the steps necessary to determine the mix ratio of the mobile phase from measurements of the mobile phase taken by the conductance sensor 20. In certain embodiments, programming is also provided for controlling the volume of fluid from a fluid reservoir, e.g., by controlling a respective pump and/or valve as described above.

As noted above, the conductance sensor 20 employs a pair of spaced-apart contacts or electrodes 22 and 24 positioned, e.g., printed directly on substrate 4, downstream from the point of introduction of the fluid to be used as the mobile phase, such that both electrodes are positioned on substrate 4 and specifically in a fluid pathway of substrate 4. In other words, both electrodes for sensing conductance are integral with the substrate 4, meaning the electrodes are positioned directly on or in the substrate. In this manner, a precise measurement of current flow between the electrodes can be obtained without interference from other sources and a separate power source need not be required. In this embodiment, a first mobile phase fluid 40 is contained in a first reservoir 45 and a second mobile phase fluid 50 is contained in second mobile phase reservoir 55 and thus the spaced-apart pair of electrodes may be positioned at a point after the first and second fluids are mixed together to provide a mobile phase that will be used to separate the constituents of a sample added to the mobile phase and the mobile phase is present in one of the fluid pathways of the apparatus. The conductance sensor is usually, though not always, downstream from the mixing element or manifold 19, if present, and usually upstream from the point of sample introduction, e.g., prior to a sample injection loop. Such a mixing element or mixing chamber may be in the form of, e.g., a laminar fluid mixer, vibrating mixer, vortex mixer and the like. As noted above, in certain embodiments, a feedback loop or rather a mobile phase fluid controller, operatively associated with the mix ratio determinator and the means employed to control the amount of fluid dispensed, is provided for adjusting, e.g., automatically, the mix ratio of the mobile phase in response to a determined mix ratio, as represented herein as dashed-lines 81 and 82. The mobile phase fluid controller includes hardware/software for adjusting the mix ratio of a mobile phase.

The electrodes that make up the conductance sensor may be any suitable electrodes. At least the surfaces of spaced—apart electrodes 22 and 24 are made of highly conductive metal. The electrodes may be formed of a number of materials, either intrinsic or doped, such as palladium, gold, platinum, copper silver, iridium, carbon, doped indium tin oxide, stainless steel and the like, and other electrometals, or a combination of such materials. The electrodes are coupled to a power supply or voltage source/controller (33) for supplying a known voltage, typically a low voltage of about one volt, across the electrodes. The voltage source is usually an alternating current source. However, a direct current voltage source may also be used in certain embodiments. The power supply that supplies voltage to the electrodes may be the same power supply employed for other functions of the apparatus or may be a different power source, but is usually the same power source used to drive other functions of the apparatus is used with the electrodes. In this manner, a separate power source is not required. In this embodiment, the power source 33 is shown integrated with the mix ratio determinator, where this is but one embodiment and it will be apparent to those of skill in the art that the power source can be any suitably located power source.

The dimensions of the electrodes may vary depending on the dimensions of the apparatus and specifically the dimensions of the fluid pathway into which the electrodes extend. While the electrodes need not have the exact same dimensions, in many embodiments, each electrode has a length that may range from about 10 µm to about 100 mm, e.g., from about 100 µm to about 50 mm, a width that may range from about 1 µm to about 5 mm, e.g., from about 10 µm to about 1 mm and the thickness that may range from about 1 nm to about 10 µm, e.g., from 10 nm to about 5 µm.

As described above, a mix ratio determinator 30 is operatively coupled to the apparatus for determining the mix ratio of the mobile phase from the current flow detected by the electrode pair. The mix ratio determinator may be external, relative to the substrate, or may be positioned on the substrate itself, for example a semiconductor device may be integral with, e.g., positioned directly on or in, the substrate. The mix ratio determinator 30 may be characterized as a processor or series of processors, e.g., a microcontroller, under the control of a suitable software program such that the processor(s) is configured to execute the steps necessary to determine the mix ratio of a given mobile phase based on the detected signal obtained by the pair of electrodes in contact with the mobile phase at some point in the fluid path and/or to time and control the amount of a particular fluid introduced to the apparatus. The terms "processor" and "microprocessor" refers to any hardware and/or software combination which will perform the functions required of it. For example, a processor of the subject invention may be in the form of one or more programmable digital microprocessors such as available in the form of a mainframe, server, or personal computer (desktop or portable). Where the processor is programmable, suitable programming can be communicated from a remote location to the processor, and/or saved in a computer program product (such as a portable or fixed computer readable storage medium, whether magnetic, optical or solid state device based). For example, a magnetic or optical disk may carry the programming, and can be read by a suitable reader communicating with the processor.

Mix ratio determinator 30 is configured to execute a mix ratio algorithm that involves receiving signals representative of current flow from the electrodes to determine the mix ratio. The conductance of the mobile phase is determined according to current flow data provided to the processor(s) as an input signal. As conductance can be a function of the pH of the mobile phase, an optional pH probe 11 may be present in a suitable location. The processor(s) then executes the steps necessary to determine the conductance based on the input current signal and, from the calculated conductance, determines the mix ratio of the mobile phase. For example, typical current levels may be in the nanoamp to picoamp range. In the practice of the subject invention, current of 30 nA may be detected and related to a mix ratio of 100% water (plus 0.1% formic acid) and a current of 15 nA may be related to a mix ratio of 3:1 water to acetonitrile, or 25% acetonitrile. Accordingly, lower current levels may be related to lower ratios of water to acetonitrile.

The measurement or value determined by the mix ratio determinator may then be communicated to a user of the apparatus via a display 35, e.g., a cathode ray display. The resulting measurements may be recorded or stored electronically in a number of ways to provide a record of the measurements. The changes in current or conductance over time, for example, may be recorded on a strip-chart recorder. Other methods of recording and storing the data may be employed. Logic microprocessor control technology may also be used in order to better evaluate the data.

Accordingly, the subject invention includes computer readable media having programming (also known as computer control logic) stored thereon for implementing the steps required to determine the mix ratio from the current flow input signal. The computer readable media may be, for example, in the form of a computer disk or CD, a floppy disc, a magnetic "hard card", a server, or any other computer readable media capable of containing data or the like, stored electronically, magnetically, optically or by other means. Stored programming embodying steps for determining the mix ratio may be transferred to a computer such as a personal computer (PC), (i.e., accessible by a researcher or the like), by physical transfer of a CD, floppy disk, or like medium, or may be transferred using a computer network, server, or other interface connection, e.g., the Internet.

More specifically, computer readable medium may include stored programming embodying an algorithm for determining the mix ratio from signal provided by the electrodes. The algorithm may also include instructions necessary to adjust the amount and/or concentration of one or more of the fluids of the mobile phase based on the determined mix ratio, i.e., provide a controlled feedback loop from the processor(s) to the reservoirs or pumps associated with a respective fluid so as to control or adjust the fluid output from a given reservoir in regards to amount of a fluid dispensed therefrom. The computer readable medium may also include reference values, e.g., in the form of a standard curve or the like, to which a particular parameter of the mix ratio determination may be compared, e.g., current flow, conductivity, etc.

Samples are typically introduced to the apparatus via an injection port such as sample injection port 115. The injection port may include an injection valve (not shown) and a sample loop (not shown). The sample is drawn into a syringe or the like and injected into the loop via the injection valve. A rotation of the valve rotor closes the valve and opens the loop in order to inject the sample into the stream of the mobile phase. Loop volumes for the subject microfluidic devices may range between about 1 nL to about 100 nL. As noted above, in certain embodiments a sample may be added to the mobile phase at an earlier location in the system, e.g., to one or more reservoirs. In many systems, sample injection may be automated.

Apparatus 2 may also include a suitable detector 9, operatively coupled to the apparatus, for detecting constituents of the eluant as the eluant exits pathway 10. Such detectors may be "on-line" or "on-chip" detectors such that a detector may be integral with substrate 4 such as detector 9 of apparatus 2 (i.e., positioned directly on or in substrate 4). In certain embodiments, a suitable detector may be a separate component from substrate 4 such that it is "off-line" or "off-chip" (i.e., a detector may not be integral with the apparatus but rather may be separated therefrom). Suitable detectors include, but are not limited to, fluorescent detectors, electrochemical detectors, mass spectrometers, UV-VIS detectors, refractive index detectors, etc. In many embodiments a detector is operatively associated with an amplifier (not shown) for amplifying the signal produced by the detector and also to a user display or readout 35 for communicating or displaying the results of the detector to a user. For example, the detector may be an optical detection window disposed across one or more fluid paths. Optical detection windows may be transparent or opaque windows such that a user is capable of viewing an optical signal from the fluid path over which they are disposed via the detection window. In other embodiments, the detector is not disposed on the apparatus itself and is instead a separate component such as a mass spectrometer wherein eluent exits the apparatus and then is transferred to a mass spectrometer for detection.

The apparatuses of the subject invention typically also include various other components such as at least one of reservoirs, pumps, valves, filters, chambers, cavities, reaction heaters, diffusers, nozzles, and the like, as are well known to those of skill in the art. For example, microfluidic valves such as microvalves 47 and 57 may control the flow of the fluid from the respective reservoirs, through the channels or between the other microfluidic components, such as the mixers, pumps, and chambers, etc. Any suitable microfluidic valve(s) may be employed with the subject invention and include those using such technologies as electrostatic, magnetic, piezoelectric, bimorph, thermo pneumatic, and pressure sensitive valves (see for example, U.S. Pat. Nos. 6,143,248; 6,158,712; 6,375,901; 6,561,224;

and 6,431,212, the disclosures of which are herein incorporated by reference). Fluids 40 and 50 may flow from the fluid sources 45 and 55, respectively, to a respective fluid pathway responsive to pressure exerted on the fluid. Regardless of the number of reservoirs employed, each may be coupled to an outgassing element 41 and 42 for degassing the fluid contained in the reservoir. The pressure exerted on the fluids 40 and 50 may be supplied from an external source or an internal source relative to the microfluidic apparatus 2. Examples of the external source of pressure include, but not limited to, gravity and rotating mechanisms. An example of the internal source of pressure includes, but is not limited to, a pump (see for example U.S. Pat. Nos. 6,533,553; 6,296, 452, the disclosures of which are herein incorporated by reference). Any suitable microfluidic pump(s) may be employed with the subject invention and include pneumatic pumps, syringe pumps, single piston pumps, rapid refill pumps, twin headed pumps, diaphragm pumps, reciprocating piston pump, constant pressure pump, and the like, where pumps suitable for use in the subject invention are described in, e.g., the above-noted patents. Inputting devices such as a keyboard or mouse optionally provide for user input, e.g., to enable a user to input or set a particular mobile fluid mix ratio or input a gradient mix ratio protocol.

The above-described microfluidic device is exemplary only and is in no way intended to limit the scope of the invention as a variety of different microfluidic devices may be employed with the subject invention (see for example U.S. Pat. No. 6,495,016 and U.S. patent Ser. No. 20030000835, the disclosures of which are herein incorporated by reference).

As described above, the subject invention is not limited to microfluidic devices. Accordingly, the subject invention also includes bench scale apparatuses characterized by a mobile phase pathway positioned on the apparatus, a pair of spaced-apart electrodes positioned within the pathway for detecting current flow within a mobile phase present in the pathway, and a mix ratio determinator coupled to the pair of electrodes for determining the mix ratio of the mobile phase based on the detected current flow.

Figure 2A:
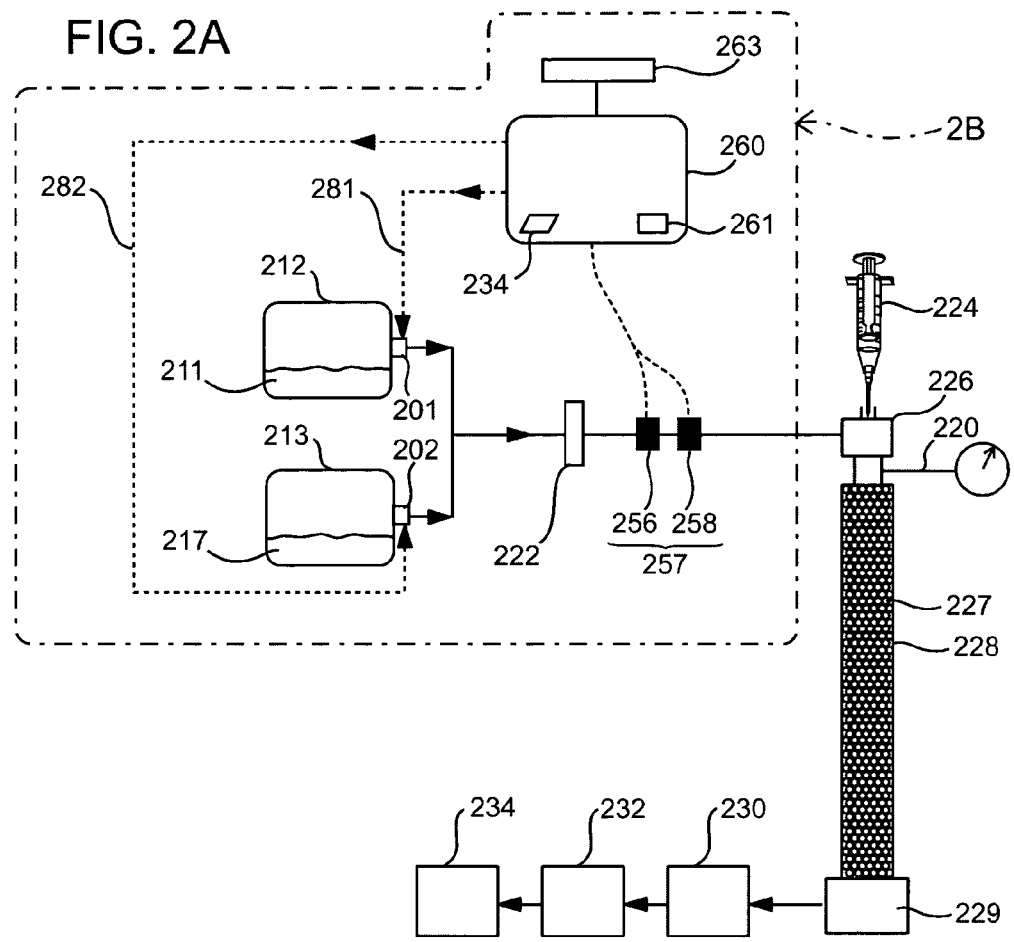
FIGS. 2A and 2B shows another exemplary embodiment of an apparatus of the subject invention.
Figure 2B:
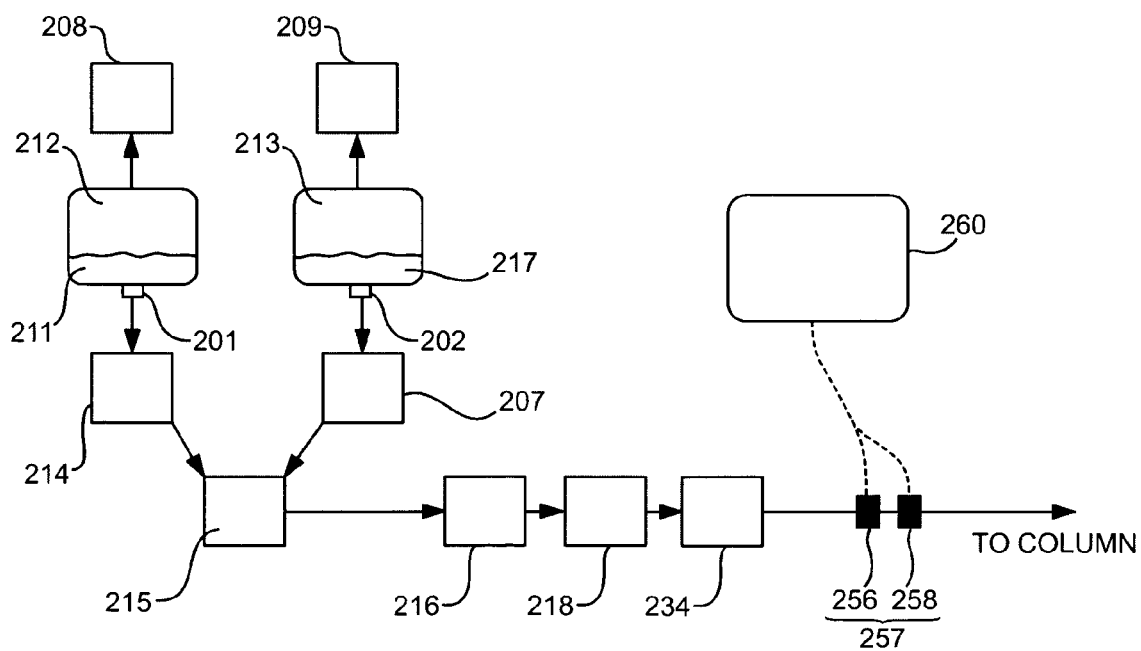

FIGS. 2A and 2B show an exemplary embodiment of a bench scale liquid chromatography apparatus according to the subject invention, e.g., an exemplary HPLC apparatus, e.g., RP-HPLC. Accordingly, the subject apparatuses may be chromatography apparatuses such that they may be configured to perform achromatography protocol such as liquid chromatography, HPLC or RP-HPLC or other chemical, physical or biological protocol such as electrophoretic or size exclusion protocol. The bench scale apparatuses of the subject invention are analogous to the microfluidic apparatuses described above and typically include a fluid delivery system, a sample injection system, e.g., a sample injection valve, a constituent process or separation column, etc., where some or part of the apparatus may be automated.

FIGS. 2A and 2B show an exemplary embodiment of an apparatus 210 according to the subject invention, where the apparatus is configure to be utilized in a chromatography protocol. FIG. 2B shows a more detailed illustration of the apparatus of FIG. 2A. As shown in FIG. 2A and 2B, apparatus 210 includes a variety of components, where some of the components may be optional (e.g., a guard column, additional reservoirs, etc.). In general, the bench-scale and microfluidic devices of the subject invention have analogous components and thus the above-described discussion relating to the microfluidic devices of the subject invention is generally applicable to the discussion below relating to the larger bench-scale devices, where differences in components, set-up, etc., will be apparent to those of skill in the art.

Analogous to the microfluidic devices of the subject invention, bench-scale apparatus 210 includes at least one fluid reservoir 212. Fluid reservoir 212 may be configured for containing a first fluid to be used in a mobile phase. In certain embodiments, only one reservoir is provided that includes the mobile phase to be used, e.g., 100% water or water mixed with at least one additional organic additive or modifier, such as methanol or the like, in a suitable proportion to the water. However, in certain embodiments, additional reservoirs are provided such as reservoir 213 for containing a second fluid to be used in a mobile phase. As described above, in this manner the proportion of the components of the mobile phase may be altered, e.g., gradually or step-wise, during a given protocol by adjusting the amount of fluid allowed to flow from a given reservoir. For example, a first reservoir such as reservoir 212 may contain a first fluid and a second reservoir may contain a second fluid such as an organic modifier such as methanol or acetonitrile or the like. In use, the fluids contained in the reservoirs may be combined in a particular proportion to be used throughout the entire separation process or may be combined in various proportions, where the proportion may vary at different times throughout the separation process such that a first fluid may be 100% water, where such may be followed by various fluids of decreasing proportions of water and increasing proportions of an organic modifier, such as 95% water and 5% organic solvent, 90% water and 10% organic solvent, etc. The constituents of interest, i.e. to be separated, may be added to the reservoirs, but are typically combined with the mobile phase at a downstream location (see sample introduction syringe or valve 224). Regardless of the number of reservoirs employed, typically each is coupled to an outgassing element 208 and 209 for degassing the fluid contained in the reservoir. An optional mixing element 215 may be included when two or more reservoirs are employed to ensure complete mixing of the components of the mobile phase.

Suitably positioned valves, e.g., valves 201 and 202 and/or suitably positioned pumps may control the flow of the fluids from the reservoirs. Any suitable valve(s) may be employed with the subject invention and include those using such technologies as electrostatic, magnetic, piezoelectric, bimorph, thermo pneumatic, and pressure sensitive capillary forces, and the like. Fluid from the reservoir(s) are typically passed through a suitable filter element 214 (and optional additional filter 207) to eliminate or substantially reduce any contaminants or elements that may be deleterious to the column or the constituents of interest. In this particular embodiment, the fluids are mixed first and then pumped, via pump 216, through a pressure relief and vent 218. A pressure gauge 220 is typically employed at a suitable location in-line, usually prior to fluid entering the separation column 228 and may also be prior to entering optional guard column 222. Pump 216 may be any suitable pump including a pneumatic pump, syringe pump, single piston pump, rapid refill pump, twin headed pump, diaphragm pump, reciprocating piston pump, constant pressure pump, etc. Usually, pump 216 provides a steady high pressure with no pulsations and may be programmed to vary the composition of the mobile phase during the course of the separation.

In many embodiments, a small "guard" column 222 may be positioned before or after the sample injection port 226, but before the analytical or separation column 228. This optional guard column 222 protects the separation column 228 against components in the mobile phase that may be harmful to the system and/or the separation process such as components that may clog the separation column 226, compounds and ions that may cause "baseline drift", decreased resolution, decreased sensitivity, and create false peaks; compounds that may cause precipitation upon contact with the stationary or mobile phase, and compounds that might co-elute and cause extraneous peaks and interfere with detection and/or quantification. Guard column 222 may be packed with the same stationary phase as separation column 228 and may be of the same inner diameter as column 228, but may be packed with a different stationary phase than separation column 228 and/or have different dimensions, e.g., a shorter length.

A temperature-regulating element 223 for use in regulating the temperature of the separation process may be coupled with the system, herein shown positioned prior to sample introduction element 226, but may be positioned in any convenient location.

As described above, a feature of the subject invention is a conductance sensor that includes at least one pair of spaced-apart electrodes suitably positioned "in-line" so as to determine the mix ratio of the mobile phase. The embodiments of FIGS. 2A and 2B show but one position where the spaced-apart pair of electrodes may be placed shown herein as spaced-apart set of electrodes 257 that includes a first electrode 256 and a second electrode 258. Of course, the spaced-apart pair of electrodes may be positioned in any suitable position and is typically at least downstream from a point where the fluids are mixed and upstream from sample introduction point. A power source or voltage source/controller 234 provides voltage to the electrodes.

Accordingly, the bench scale apparatuses of the subject invention also include elements for the determination of the mix ratio of the mobile phase. Such as a conductance sensor such as sensor 250 that is operatively coupled to a mobile phase mix ratio determinator 260 which includes a processor or series of processors 261 under the control of a computer program which directs the processor(s) to execute the steps necessary to determine the mix ratio of the mobile phase from measurements of the mobile phase taken by the conductance sensor. The measurement or value determined by the mix ratio determinator may then be communicated to a user of the apparatus via a display 35, e.g., a cathode ray display.

As noted above, the spaced-apart pair of electrodes of the conductance sensor employs a pair of spaced-apart contacts or electrodes 252 and 254 are positioned downstream from the point of introduction of the mobile phase fluids. In this embodiment, a first mobile phase fluid 211 is contained in a first reservoir 212 and a second mobile phase fluid 217 is contained in second mobile phase reservoir 213 and thus the spaced-apart pair of electrodes may be positioned at a point after the first and second fluids are mixed together to provide a mobile phase that will be used to separate the constituents of a sample added to the mobile phase. The conductance sensor is usually, though not always, downstream from an optional mixing element or chamber 215, if present, and usually upstream from the point of sample introduction. Such a mixing element or mixing chamber may be in the form of, e.g., a laminar fluid mixer, vibrating mixer, vortex mixer and the like. In certain embodiments, a feedback loop is provided for adjusting, e.g., automatically, the mix ratio of the mobile phase in response to a determined mix ratio, as represented herein as dashed-lines 281 and 282.

Analogous to that described above for the microfluidic devices of the subject invention, the conductance sensor or the electrodes of the electrode pair are positioned on the apparatus itself, and specifically across a mobile phase fluid pathway so that a volume of a mobile phase present in the fluid pathway contacts or rather flows between the electrodes. In this manner, a precise measurement of current flow between the electrodes can be obtained without interference from other sources and a separate power source need not be employed. The material of the electrodes of the apparatus 210 will generally be the same as that described above. The dimensions of the electrodes may vary depending on the dimensions of the bench-scale apparatus and specifically the dimensions of the fluid pathway into which the electrodes extend. While the electrodes need not have the exact same dimensions, in many embodiments the electrodes will be about 10 μm to about 250 μm in width and spaced from about 10 μm to about 1000 μm apart. Length of an electrode is generally whatever length is necessary to connect to wires leading to the determinator, e.g., about 1 mm to about 10 mm. For example, each electrode may have a length that may range may range from about 10 μm to about 100 mm, e.g., from about 100 μm to about 50 mm, a width that may range from about 1 μm to about 5 mm, e.g., from about 10 μm to about 1 mm and the thickness that may range from about 1 nm to about 10 μm, e.g., from about 10 nm to about 5 μm.

As described above, a mix ratio determinator 260 is operatively coupled to the apparatus for determining the mix ratio of the mobile phase from the current flow detected by the electrode pair and may be either external relative to the apparatus or may be positioned on the apparatus. Analogous to that described above, the mix ratio determinator 260 may be characterized as a processor or series of processors, e.g., a microcontroller, under the control of a suitable software program such that the processor(s) is configured to execute the steps necessary to determine the mix ratio of a given mobile phase based on the detected signal obtained by the pair of electrodes in contact with the mobile phase at some point in the fluid path and/or to time and control the amount of a particular fluid introduced to the apparatus.

Samples are typically injected into the system via an injection port 226. The injection port of the subject apparatuses usually includes an injection valve and a sample loop (not shown). The sample is drawn into a syringe 224 or the like and injected into the loop via the injection valve. A rotation of the valve rotor closes the valve and opens the loop in order to inject the sample into the stream of the mobile phase. Loop volumes may range between about 1 μl to about 100 ml or more, where in many embodiments the loop volumes may be less than about 1 μl or more than about 100 ml. As noted above, in certain embodiments a sample may be added to the mobile phase at an earlier location in the system, e.g., to one or more reservoirs. In many systems, sample injection may be automated.

As shown, separation column 228 includes the stationary phase 227 of the subject invention. Separation column 228 may be fabricated from any suitable material such as glass, stainless steel or plastic. The dimensions of column 228 may vary depending on a variety of factors relating to a particular separation process, e.g., the constituents of interest, the stationary phase, the mobile phase, etc. For example, a column may have a length that ranges from about 5 mm to about 3000 cm, usually from about 10 mm to about 300 mm and more usually from about 50 mm to about 300 mm, and an internal diameter or width that ranges from about 0.01 mm to about 250 cm or more, usually from about 0.1 mm to about 8 mm and more usually from about 0.1 mm to about 4.6 mm. Of course, columns having dimensions other than those described above may also be employed. The separation column usually, though not necessarily, includes end fittings (not shown) at one or both ends of the column that connects the column to the sample injector and/or detector. Oftentimes such endfittings include a frit to hold or contain the stationary phase in a suitable packing configuration (e.g., a dense packing configuration), where such frits may be made from any suitable porous material such as stainless steel or other inert metal or plastic such as PTFE or polypropylene.

Apparatus 210 also includes a suitable detector 229 for detecting constituents of the eluant as the eluant exits column 28, herein shown integral with apparatus 210. In those embodiments where the detector is a separate component from the apparatus, as described above, the conductance sensor is positioned on the apparatus and thus the detector does not include one or both of the electrodes of the spaced-apart electrode pair. In this manner, the conductance sensor does not require a separate power source from that used with the apparatus. As noted above, suitable detectors include mass spectrometers, UV-VIS detectors, refractive index detectors, fluorescent detectors, electrochemical detectors, etc. In many embodiments detector 229 is operatively associated with an amplifier 230 for amplifying the signal produced by the detector and also to a user interface or readout 232 for communicating or displaying the results of the detector to a user. The apparatus may be operatively coupled to a data collection unit such as a computer 234 which may be integrated with one or more components of the apparatus, i.e., a unitary piece of construction, or may be a separate component.

Systems

Also provided are systems for separating at least two constituents present in a mobile phase. The systems include an apparatus of the subject invention and a mobile phase that includes at least two fluids.

The fluids that make-up a given mobile phase may vary depending on the particular protocol being performed. Accordingly, a variety of fluids may be employed in the subject invention. In many embodiments, the fluids are chosen based in part on their relative polarities with respect to the stationary phase and/or with respect to each other. For example, in normal phase chromatography protocols, the stationary phase is relatively polar and the mobile phase is chosen to be relatively non-polar and thus a first fluid may be substantially non polar and a second fluid may be relatively polar where the two fluids are employed, e.g., combined in varying proportions, throughout a protocol to provide a mobile phase having varying degrees of polarity. In reversed phase protocols, the first fluid is usually chosen to be the more polar fluid, e.g., water, relative to a second, less polar and more organic fluid such as, e.g., acetonitrile or methanol, etc.

A given mobile phase may include one, two, three or more fluids which may be used alone or in combination with one or more of the other fluids to provide a given mobile phase. For example, embodiments may include at least a first fluid and a second fluid such that the mobile phase employed may include varying proportions of each fluid such as about 100% of the first fluid and about 0% of the second fluid, followed by lesser percentages of the first fluid and corresponding greater percentages of the second fluid such that the mobile phase may transition to one having about 0% of the first fluid and about 100% of the second fluid. Third, fourth, fifth, etc., fluids may also be incorporated into a protocol in a manner analogous to that described above using two fluids.

Depending on the particular protocol being performed, the pH of the individual fluids, as well as the pH of the mix of any two or more fluids (i.e., the mobile phase) will vary and may be acidic, neutral or basic such that the pH may range from 1–14. As a variety of different fluids may be employed with the subject systems depending on the particular analytical protocol being performed, the fluids may be polar, non-polar, organic, inorganic, etc. Fluids of interest include, but are not limited to, water (i.e., 100% water), and water-based fluids, methanol, heptafluorobutyric acid (HFBA), acetonitrile, formic acid, N,N'-diethylamine (DEA), tetrahydrofuran, trifluoroacetic acid (TFA), acetone, dichloromethane, hexane, n-heptane, propanol, ethanol, isopropanol, and the like.

Various other components or additives may be included with one or more fluids or may be added to the mobile phase subsequent to the mixing of two or more fluids in a particular proportion where such components include, but are not limited to, surfactants, a suitable buffering system, and the like.

Other components of the subject system may include, but are not limited to, fraction collectors and analyte detectors if not integrated with the subject apparatus, i.e., if not positioned directly on the microfluidic apparatus or the separation column itself.

Methods

As summarized above, methods are provided that include contacting a mobile phase with an apparatus for separating constituents of a mobile phase, detecting the current flow of the mobile phase when in contact with the apparatus and determining the mix ratio of the mobile phase from the detected current flow. In certain embodiments the mix ratio is adjusted, e.g., automatically under the direction of a suitable software program, in response to the determined mix ratio. Accordingly, a feature of the subject methods is the mix ratio of the mobile phase can be determined while the mobile phase is present in a fluid pathway of a separation apparatus, e.g., prior to adding a sample to the mobile phase. In this manner, the mix ratio may be determined, and in certain embodiments adjusted or optimized, in real time. This feature enables direct monitoring and precise control over the mix ratio during a protocol.

The subject methods are generally described by the flowchart of FIG. 3. As shown in FIG. 3, a first step of the subject methods includes contacting a mobile phase 301 with a constituent separation apparatus, and in particular a fluid pathway of such an apparatus. The mobile phase may be made of one, two, or three or more different fluids. Contacting of the mobile phase or the individual fluids of the mobile phase may be accomplished in a number of ways which include manual, e.g., direct pipetting, etc., and semi- or completely automated techniques such as employing automated fluid reservoirs, pumps, valves, and the like. As described above, two or more fluids (herein shown as two fluids in this embodiment) may make-up a given mobile phase and thus the subject invention includes contacting a suitable amount of at least a first fluid and a second fluid with the apparatus to provide a mobile phase of a particular mix ratio of the two fluids. The first and second fluids may be mixed prior to contact with the apparatus or may be contacted separately and then mixed together. For example, in the instances where the apparatus is a microfluidic device, each fluid may be contacted with a respective fluid pathway wherein the fluid pathways join at some point to provide a mix of the fluids.

The amount and flow rate of each fluid used in a given protocol will vary depending of the particular protocol being performed, and may change over the course of a protocol. In those embodiments employing a microfluidic apparatus employing a mobile phase made up of two fluids, in general the amount of each fluid employed over the course of a given protocol may range from 0.01 μL to about 1 mL, e.g., from about 0.1 μL to about 100 μL, e.g., from about 0.3 μL to about 30 μL, where the flow rate may range from about 100 nL/minute to about 1000 nL/minute. In those embodiments employing a larger apparatus (i.e., a bench scale apparatus) employing a mobile phase made of two fluids, in general the amount of each fluid employed over the course of a given protocol may range from about 100 μL to about 1 L where the flow rate may range from about 10 μL/minute to about 100 mL/minute. The above-described ranges are exemplary only and are in no way intended to limit the scope of the subject invention as the ranges vary depending on, e.g., whether more than two fluids are employed, etc.

As shown in FIG. 3, once a mobile phase of a particular mix ratio is present on a suitable separation apparatus, a conductance sensor measures the conductance of the mobile phase 305 and more specifically the mobile phase is passed across a conductance sensor and more specifically passed through a pair of spaced-apart pair of electrodes 302 in order to obtain information related to conductivity. The mobile phase is typically maintained at a suitable temperature, where the temperature may range from about 4° C. to about 40° C. The pair of electrodes is configured, i.e., sized, shaped, spaced-apart, etc., to enable current flow to be detected therebetween. As described above, in accordance with the subject invention, the placement of the electrodes on a particular separation apparatus may vary with the limitation that both electrodes are positioned directly on the apparatus itself, i.e., in a fluid pathway of an apparatus. Typically, as noted above, the electrodes are positioned at a location upstream or rather prior to the introduction of sample to the mobile phase. In this manner, the mix ratio may be monitored, and in many embodiments adjusted, before sample is added thus conserving sample in those instances where the mix ratio is incorrect or requires adjustment.

A suitable voltage is applied across the electrodes 303 where the amount of voltage applied will vary depending on a variety of factors such as the size of the particular electrode pair, the amount of fluid flowing between the electrodes for a given time point, the size of the fluid pathway, etc. For example, for a microfluidic apparatus having dimensions described above, the voltage may range from about 100 mV to 2 V and for a bench scale apparatus having dimensions described above, the voltage may range from about 100 mV to 2 V Because the electrodes are integrated with the separation apparatus itself, voltage may be supplied from the power supply of the separation apparatus itself and thus a separate power supply need not be required.

As voltage is applied, and mobile phase is present, between the electrodes, the current flow through the mobile phase is detected between the electrodes 304. Current flow measurements may be made at least every second, where in certain embodiments the current flow measurements may be made every fraction of a second, e.g., every 0.1 second, etc. Accordingly, the time period for detecting the current flow may range from about every 0.1 second to about every 10 seconds.

The measured current flow signals or data values are then manipulated to determine the electrical conductivity of the mobile phase 305. This conductance measurement is characteristic of the mix ratio of the mobile phase and thus from the conductivity measurement, the mix ratio of the mobile phase is determined 306. Generally, the conductance is a function of the ionic molecules present in the mobile phase, which ionic species are conductors. More specifically, the determined conductivity is proportional to the concentration of dissolved and dissociated ionic species in the mobile phase. Because the extent of dissociation of ionic species is dependant upon the mix ratio of the fluids of the mobile phase, e.g., the relative proportions of a first aqueous fluid and second organic solvent, and since the identity of the dissolved ionic species is known (as well as the temperature of the solution), the mix ratio is determined from the conductivity measurement. Such determination may be accomplished with the use of standards or references such as calibration curves such that the conductivity of a given mobile phase may be compared to a standard curve to determine the mix ratio. Once the mix ratio is determined, it may be communicated to a user and/or recorded on a recordable substrate, e.g., in the form of a chart recorder, graphical representation, etc.

Representative current values, respective conductivity values and mix ratios determined using these values include, but are not limited to, 0 to 30 nA, 0 to 1000 μS/cm and 0 to 100% organic solvent.

In many embodiments, the measured conductivity is used in a feedback loop 307 to control the metered volumes of the fluids of the mobile phase such that the metered volumes of a first fluid may be altered 308 and/or the metered volumes of a second fluid may be altered 309 based on the determined mix ratio. In certain embodiments employing a gradient elution protocol (gradual or step-wise), the amounts of one or more fluids is changed over the course of the protocol, e.g., to provide a mobile phase of decreasing polarity over the course of the protocol such that a steady change of eluent strength is employed for a separation, e.g., one or more successive eluents may have increasing strengths such that they may include water and increasing amounts of a less polar solvent. Accordingly, the subject invention provides a means to monitor and precisely control the grading of the mobile phase.

In accordance with the subject methods, constituents may be combined with the mobile phase and processed, separated, etc., and in certain embodiments a plurality of sample may be processed or separated in parallel. Accordingly, prior to being contacted with a processing or separation component of the apparatus, i.e., the stationary phase, matrix, and the like, constituents of interest, i.e., the constituents to be separated, may be added to or otherwise combined with the mobile phase, where the constituents may be processed prior to such combining. The constituents may be included in a sample, where the term "sample" as used herein relates to a material or mixture of materials, typically, although not necessarily, in fluid form, containing one or more constituents of interest. A sample may be any suitable sample that includes a constituent of interest, where the sample and/or the constituent may be pre-processed prior to separation, e.g., may be amplified, denatured, fractionated, etc. Representative samples may include, but are not limited to, biological fluids such as blood, cell suspensions, protein solutions, serum, urine, tears, etc., as well as non-biological fluids such as water, buffer and the like.

In such embodiments, once the constituent(s) of interest is combined with the mobile phase, the constituent-containing mobile phase is contacted with the reaction region or compartment, e.g., a separation compartment, of the apparatus under conditions sufficient to isolate at least one of the constituents present in the mobile phase. In this manner, one or more constituents are bound or otherwise retained for a period of time by the reaction compartment, e.g., retained by a stationary phase. The one or more bound constituents are then eluted from, e.g., the stationary phase, by employing a suitable mobile phase designed for this elution which may include varying the proportions of the fluids of the mobile phase. For example, in those embodiments that employ a mobile phase gradient that increases in concentration of an organic modifier (e.g., acetonitrile or methanol) relative to water as described above, the protocol may be designed to elute the constituent molecules in order of increasing hydrophobicity by increasing the amount of the organic modifier relative to the amount of water.

Typically, the constituent-containing mobile phase is flowed over or through a reaction region, e.g., a stationary phase, at a flow rate that is suitable for the particular constituent processing, separation, etc., where the flow rate falls within the ranges described above.

The amount or volume (i.e., the elution volume or $V_R$) of the mobile phase required to elute one or more constituents from the reaction component will vary depending on the particulars of the mobile phase, constituent(s) to be eluted, etc. Typically, the elution volume ranges from about $10^{-9}$ L to $10^{-6}$ L for a microfluidic device and about $10^{-6}$ L to 1 L for a benchtop device (e.g., depending on the size of the chromatographic column).

Once eluted, the eluate or effluent (i.e., the combination of the mobile phase and constituents exiting the stationary phase) is detected by a suitable detector, where a variety of detectors are known for such detection. Such detectors include ultraviolet (UV-VIS) detectors wherein the eluate is irradiated with a light source and the amount of light that passes from the light source, through the eluate and to the detector, is measured. Refractive index reflectors may also be employed wherein the detector measures the deflection of light by the eluate, where each constituent has a unique refraction index. Electrochemical detectors may also be employed in certain embodiments, wherein an electrochemical detector responds to analytes that can be oxidized or reduced at an electrode over which the eluate passes. In this manner, electric current through the electrode increases in proportion to the amount of constituent in the eluate. Also of interest are fluorescent detectors which respond to constituents in the eluate that fluoresce. In using such a fluorescent detector, the eluate is irradiated and the emission wavelengths are measured wherein the emission intensities are proportional to the amount of constituent in the eluate. Mass spectrometers may also be employed to detect and analyze separated constituents. Accordingly, the presence of constituents in the eluate may be recorded by mass spectroscopy, by detecting a change in UV-VIS absorption at a set wavelength, by refractive index, by fluorescence after excitation with a suitable wavelength, by electrochemical response, and the like. Regardless of the type of detector employed, typically the results of the detector is communicated to a user via a suitable user interface or readout. In many embodiments, the one or more constituents are detected "on-line" or rather on the separation apparatus itself instead of being transferred to a remote location for detection.

Some or all of the various steps of the subject invention may be implemented in part or in whole using computer-based systems and methods, as described above. Accordingly, some or all of the subject methods may be accomplished by the use of suitable computer programming, where such may be recorded on a computer readable medium.

In certain embodiments, the subject methods include a step of transmitting data from at least one of the steps of the subject methods, as described above, to a remote location. For example, such transmitted data may be related to a determined mix ratio (e.g., detected current flow, determined conductivity, determined mix ratio, detected constituent(s), and the like). By "remote location" is meant a location other than the location at which the method step occurs, e.g., a location other than the location at which a separation apparatus is located. For example, a remote location could be another location (e.g., office, lab, etc.) in the same city, another location in a different city, another location in a different state, another location in a different country, etc. As such, when one item is indicated as being "remote" from another, what is meant is that the two items are at least in different offices, labs or buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, Internet, etc.

As such, in performing the subject methods, an apparatus for isolating constituents is contacted with a mobile phase and the mix ratio of the mobile phase is determined when the mobile phase is in contact with the apparatus and constituents present in mobile phase may be detected. Results relating to the mix ratio determination and/or constituent detection may be raw results (such as current flow signal intensity, fluorescence intensity readings for the one or more detected constituents, etc.) or may be processed results such as forming conclusions based on the determination (such as the mix ratio, whether or not a particular constituent may have been present, etc.). The results of the determination and/or detection (processed or not) may be forwarded (such as by communication) to a remote location if desired, and received there for further use (such as further processing).

Utility

The above-described methods and apparatuses to practice the same may be used in a variety of applications that employ a fluid or mobile phase in the protocol, e.g., for the separation, preparation and identification of samples of nucleic acids, proteins, carbohydrates, the identification of a particular analyte in a complex mixture, and the like, which protocols find use in a variety of fields in both basic research and industrial processes, including analytical, biomedical, pharmaceutical, environmental, molecular, biological, food and clinical applications. For example, applications include, but are not limited to, separation or isolation of a constituent (e.g., electrophoretic, chromatographic, etc.,) isoelectric focusing, immunoassays, flow cytometry, PCR amplification, nucleic acid analysis, cell separation, (see for example, Hadd, et al., Microchip device for performing enzyme assays. Analytical Chemistry 69, 3407–3412 (1997); Macounova, et al. Concentration and separation of proteins in microfluidic channels on the basis of transverse IEF. Analytical Chemisty 73, 1627–1633 (2001); Bucholz, et al.

Microchannel DNA sequencing matrices with a thermally controlled "viscosity switch". Analytical Chemisty 73, 157–164 (2001)). Representative applications in which the subject invention may find use are described, e.g., in U.S. Pat. Nos. 5,770,029; 5,755,942; 5,746,901; 5,681,751; 5,658,413; 5,653,939; 5,653,859; 5,645,702; 5,605,662; 5,571,410; 5,543,838; 5,480,614; the disclosures of which are herein incorporated by reference.

Kits

Finally, kits for use in practicing the subject methods are provided. The subject kits include at least an apparatus for separating constituents and instructions for using the apparatus in the practice of the subject methods. The instructions that are provided with the subject kits are generally recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions may be recorded on a suitable substrate.

The subject kits may also include at least some, if not all, of the components for preparing a mobile phase. As such, the kits may include one or more containers such as vials or bottles, with each container containing a separate component of a mobile phase. For example, a kit may include a prepared mobile phase, e.g., water and a modifier, or may include one or more components to prepare such a mobile phase such as one or more of: HPLC grade water, HPLC grade organic modifier, such as methanol, acetonitrile, propanol, ethanol, isopropanol, etc. In addition, the kits may include one or more additional elements that find use in the particular application for which the invention is used, where such elements include, but are not limited to: elements used in electrophoretic or chromatographic applications, such as a separation medium, labels for use in separation, buffer mediums, and other reagents for practicing electrochromatographic protocols; etc.

Programming embodied on a computer readable medium, as described above, may also be included in the subject kits. Accordingly, programming present on a computer readable medium for carrying out some or all of the subject methods may be included in a subject kit

EXPERIMENTAL

The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

I. On-Chip Mobile Phase Conductivity Using a Microfluidic Apparatus: Gradient Mobile Phase Two spaced-apart electrodes positioned directly in a fluid pathway of a microfluidic apparatus were employed to measure the conductivity of a gradient mobile phase elution. The electrodes are gold traces printed directly on the polyimide substrate and are each 200 µm in width, spaced 200 µm apart.

Two mobile phase fluids were used: (1) mobile phase fluid A made of 0.1% formic acid in water, and (2) mobile phase fluid B made of 0.1% formic acid in acetonitrile. The protocol included a gradient of 0–100% B from 0 to 20 minutes, reset to 0% at 20.1 minutes. The flow rate was 300 nL/min.

FIG. 4 shows the results of this protocol whereby the gradient change in mobile phase is observed by the respective conductivity. As shown, the conductivity was effectively determined for the various mix ratios of mobile phase. Specifically, the different mix ratios provided detectable conductivity characteristics.

II. On-Chip Mobile Phase Conductivity Using a Microfluidic Apparatus: 85–90% $CH_3CN$ in 1% Steps Two spaced-apart electrodes positioned directly in a fluid pathway of a microfluidic apparatus were employed to measure the conductivity of a mobile phase employed in stepwise elution protocol. The electrodes are gold traces printed directly on the polyimide substrate and are each 200 µm in width, spaced 200 µm apart.

Two mobile phase fluids were used: (1) mobile phase fluid A made of 0.1% formic acid in water, and (2) mobile phase fluid B made of 0.1% formic acid in acetonitrile. The protocol included 1% increments of mobile phase fluid B added every five minutes beginning at zero minutes. The flow rate was 300 nL/min.

FIG. 5 shows the results of this protocol whereby the stepped changes in mobile phase are observed by the conductivity. As shown, the conductivity was effectively determined for the various mix ratios of mobile phase. Specifically, the different mix ratios provided detectable conductivity characteristics.

III. On-Chip Mobile Phase Conductivity Using a Microfluidic Apparatus: Determination of Injection Loop Volume Two spaced-apart electrodes positioned directly in a fluid pathway of a microfluidic apparatus were employed to measure the conductivity of a mobile phase in order to determine the volume of fluid injected into the mobile phase. The electrodes are gold traces printed directly on the polyimide substrate and are each 200 µm in width, spaced 200 µm apart.

0.1% formic acid in water was used as the mobile phase. The flow rate was 300 nL/min. In this protocol, a volume of deionized water was injected into the mobile phase. The conductivity of the mobile phase over time, which included the mobile phase with and without the injected deionized water, was determined. The injected volume of deionized water was calculated from the area of the (inverse) peak.

FIG. 6 shows the results of this protocol whereby the injection of deionized water produces a detectable drop in conductance. The magnitude of this conductance change was used to determine the volume of deionized water injected.

It is evident from the above results and discussion that the above described invention provides important new apparatuses and methods for determining the mix ratio of a mobile phase. Specifically, the subject invention provides methods and apparatuses that determine the mix ratio of a mobile phase directly on a separation apparatus itself, are easy to use, and have a high degree of precision. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An apparatus for separating constituents of a mobile phase, said apparatus comprising:
    (a) a fluid pathway positioned on said apparatus;
    (b) a pair of spaced-apart electrodes positioned within said fluid pathway for detecting current flow within a mobile phase when present in said fluid pathway; and
    (c) a mix ratio determinator coupled to said pair of electrodes for determining the mix ratio of said mobile phase based on said detected current flow.

2. The apparatus of claim 1, wherein said pair of electrodes is positioned to detect said current flow prior to the separation of said constituents.

3. The apparatus of claim 1, wherein said pair of electrodes is positioned to detect said current flow subsequent to the separation of said constituents.

4. The apparatus of claim 1, wherein said pair of electrodes is positioned to detect said current flow prior to the introduction of said constituents to said mobile phase.

5. The apparatus of claim 1, wherein said pair of electrodes is positioned to detect said current flow subsequent to the introduction of said constituents to said mobile phase.

6. The apparatus of claim 1, further comprising a mobile phase fluid controller operatively coupled to said mix ratio determinator for adjusting said mix ratio of said mobile phase based on said determined mix ratio.

7. The apparatus of claim 6, further comprising a first adjustable reservoir for dispensing a first mobile phase fluid to said fluid pathway and a second adjustable reservoir for dispensing a second mobile phase fluid to said fluid pathway.

8. The apparatus of claim 7, wherein the amount of fluid dispensed from at least one of said adjustable reservoirs is automatically adjusted by said mobile phase fluid controller.

9. The apparatus of claim 1, further comprising a constituent detector operatively associated with said apparatus.

10. The apparatus of claim 9, wherein said constituent detector is integral with said apparatus.

11. The apparatus of claim 1, wherein said apparatus is a liquid or capillary chromatography apparatus.

12. The apparatus of claim 11, wherein said apparatus is a microfluidic device.

13. A system for separating constituents of a mobile phase, said system comprising:
    (a) an apparatus comprising:
        (i) a fluid pathway positioned on said apparatus,
        (ii) a pair of spaced-apart electrodes positioned within said fluid pathway for detecting current flow within a mobile phase when present in said fluid pathway, and
        (iii) a mix ratio determinator coupled to said pair of electrodes for determining the mix ratio of said mobile phase based on said detected current flow,
    (b) at least a first fluid reservoir for introducing a first fluid to said apparatus and a second fluid reservoir for introducing a second fluid to said apparatus.

14. The system of claim 13, wherein said pair of electrodes is positioned to detect said current flow prior to the separation of said constituents.

15. The system of claim 13, wherein said pair of electrodes is positioned to detect said current flow subsequent to the separation of said constituents.

16. The system of claim 13, wherein said apparatus further comprises a mobile phase fluid controller operatively coupled to said mix ratio determinator for adjusting said mix ratio of said mobile phase based on said determined mix ratio.

17. The system of claim 13, wherein said first and second reservoirs are adjustable.

18. The system of claim 17, wherein the amount of fluid dispensed from at least one of said adjustable reservoirs is automatically adjusted by said mobile phase fluid controller.

19. The system of claim 13, further comprising a constituent analyzer integral with said apparatus.

20. The system of claim 13, wherein said apparatus is a liquid or capillary chromatography apparatus.

21. The system of claim 13, wherein said apparatus is a microfluidic device.

22. The system of claim 13, further comprising at least a first fluid and a second fluid.

23. The system according to claim 13, wherein said first fluid is an aqueous fluid and said second fluid is an organic fluid.

24. A method for determining a mixed ratio of a mobile phase comprising:
    (a) contacting the mobile phase with an apparatus for separating constituents of a mobile phase;
    (b) detecting the current flow of said mobile phase when in contact with said apparatus;
    (c) determining the mix ratio of said mobile phase based on said detected current flow.

25. The method of claim 24, wherein said detecting is accomplished by a pair of spaced-apart electrodes positioned on said apparatus.

26. The method of claim 24, further comprising adjusting the mix ratio of said mobile phase based on said determined mix ratio.

27. The method of claim 26, wherein said mobile phase comprises constituents and said method further comprises separating said constituents.

28. The method of claim 27, wherein said constituents are separated prior to said detection step (c).

29. The method of claim 27, wherein said constituents are separated subsequent to said detection step (c).

30. The method of claim 24, wherein said apparatus is a microfluidic device.

31. An algorithm for carrying out the method of claim 24 present on a computer-readable medium.

32. An algorithm for carrying out the method of claim 26 present on a computer-readable medium.

* * * * *